United States Patent
Stelter et al.

(10) Patent No.: US 12,279,975 B2
(45) Date of Patent: Apr. 22, 2025

(54) VOLUME-ADAPTABLE BREAST PROSTHESIS

(71) Applicant: AMOENA MEDIZIN-ORTHOPÄDIE-TECHNIK GMBH, Raubling (DE)

(72) Inventors: Nils Stelter, Frasdorf (DE); Helmut Wild, Stephanskirchen (DE)

(73) Assignee: AMOENA MEDIZIN-ORTHOPÄDIE-TECHNIK GMBH, Raubling (DE)

( * ) Notice: Subject to any disclaimer, the term of this patent is extended or adjusted under 35 U.S.C. 154(b) by 723 days.

(21) Appl. No.: 17/421,529

(22) PCT Filed: Nov. 6, 2019

(86) PCT No.: PCT/EP2019/080432
§ 371 (c)(1),
(2) Date: Jul. 8, 2021

(87) PCT Pub. No.: WO2020/143941
PCT Pub. Date: Jul. 16, 2020

(65) Prior Publication Data
US 2022/0062008 A1   Mar. 3, 2022

(30) Foreign Application Priority Data
Jan. 10, 2019   (DE) ............ 20 2019 100 103.8

(51) Int. Cl.
*A61F 2/52* (2006.01)

(52) U.S. Cl.
CPC ........ *A61F 2/52* (2013.01); *A61F 2250/0003* (2013.01); *A61F 2250/0013* (2013.01)

(58) Field of Classification Search
CPC .............. A61F 2002/523; A61F 2/52; A61F 2250/0003; A61F 2250/0013
See application file for complete search history.

(56) References Cited

U.S. PATENT DOCUMENTS

| | | | |
|---|---|---|---|
| 2,698,436 A | 1/1955 | Bernhardt | |
| 3,852,833 A * | 12/1974 | Koneke | A61F 2/52 623/7 |
| 3,934,274 A * | 1/1976 | Hartley, Jr. | A61F 2/12 450/38 |
| 5,700,288 A * | 12/1997 | Eaton | A41C 3/148 450/55 |

(Continued)

FOREIGN PATENT DOCUMENTS

| | | | | |
|---|---|---|---|---|
| CA | 2301445 A1 * | 8/2001 | | A61F 2/52 |
| DE | 102014006313 A1 | 11/2015 | | |

(Continued)

*Primary Examiner* — Suzette J Gherbi
(74) *Attorney, Agent, or Firm* — Dilworth & Barrese, LLP.

(57) ABSTRACT

The invention relates to a breast prosthesis having an adaptable volume, wherein the breast prosthesis has a first shell body, a second shell body peripherally connected thereto, and a fluid space arranged between the shell bodies, and wherein in accordance with the invention the breast prosthesis further comprises a valve tube that is composed of a flexible material and that reaches from the outside into the fluid space in the connection region between the shell bodies and projects beyond the connection region in the fluid space.

7 Claims, 5 Drawing Sheets

(56) References Cited

U.S. PATENT DOCUMENTS

| | | | |
|---|---|---|---|
| 6,936,068 B1 * | 8/2005 | Knisley | A61F 2/52 623/7 |
| 2002/0193878 A1 * | 12/2002 | Bowman | A61F 2/52 623/7 |
| 2021/0346177 A1 * | 11/2021 | Stelter | A61F 2/5044 |
| 2021/0346178 A1 * | 11/2021 | Stelter | A61F 2/52 |
| 2022/0047379 A1 * | 2/2022 | Wild | A61F 2/12 |
| 2022/0062008 A1 * | 3/2022 | Stelter | A61F 2/52 |
| 2022/0079779 A1 * | 3/2022 | Stelter | A61F 2/52 |

FOREIGN PATENT DOCUMENTS

| | | |
|---|---|---|
| DE | 102017116397 A1 | 1/2019 |
| DE | 102018125897 A1 | 4/2020 |
| DE | 102018126035 A1 | 4/2020 |
| EP | 3431047 A1 | 1/2019 |
| WO | 2020/079049 A1 | 4/2020 |
| WO | 2020/079172 A1 | 4/2020 |

* cited by examiner

Figure 3a     Figure 3b     Figure 3c
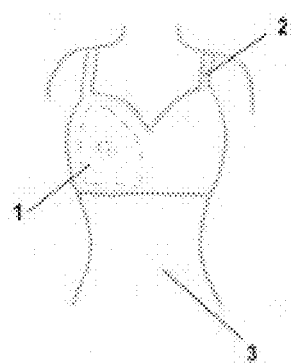 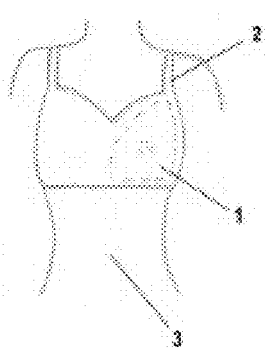 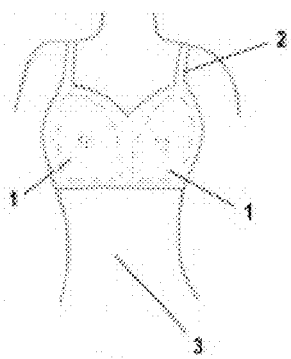
Figure 4
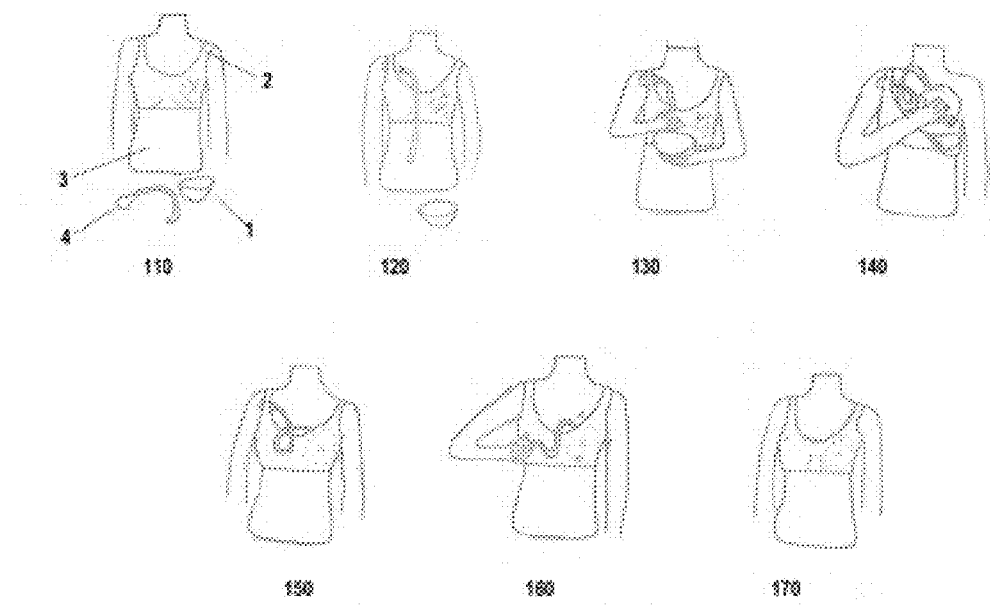

VOLUME-ADAPTABLE BREAST PROSTHESIS

BACKGROUND OF THE INVENTION

The invention relates to a breast prosthesis or a breast epithesis having an adaptable volume.

Breast prostheses are worn after surgical breast removals. Demands on breast prostheses in particular include a shape and feel that come as close as possible to the natural breast as well as a high comfort in wear.

To be able to accomplish being able to adapt the volume of such a prosthesis to the individual needs of the wearer that result from the size of the still healthy breast, if present, or from personal well-being without expensive custom-made solutions, it has already been proposed in the prior art to provide breast prostheses whose volume can be retroactively adapted. EP 2 554 138 A1 or EP 0 824 001 A2 can be named as examples for this.

SUMMARY OF THE INVENTION

It is the object of the invention to provide a volume-adaptable breast prosthesis having improved properties.

Against this background, the invention relates to a breast prosthesis having an adaptable volume, wherein the breast prosthesis has a first shell body, a second shell body peripherally connected thereto, and a fluid space arranged between the shell bodies, and wherein the breast prosthesis further comprises a valve tube that is composed of a flexible material and that reaches from the outside into the fluid space in the connection region between the shell bodies and projects beyond the connection region into the fluid space.

The shell bodies are typically themselves flexible in order, on the one hand, to be able to satisfy the demands on haptics and comfort in wear and, on the other hand, to permit an expansion of the fluid space volume. The peripheral connection between the shell bodies typically takes place by adhesive bonding or welding along the common peripheral surface. The tube can pass through this weld seam or adhesive seam in the radial direction and can be adhered or welded between the shell bodies in this process.

Provision is preferably made that the first shell body, the second shell body, or both shell bodies are film bags filled with a deformable material. The deformable material is preferably a crosslinked two-component silicone rubber. The film bags can be produced from two film pieces that are connected, preferably welded, to one another, along the common peripheral surface.

In an embodiment variant, the section of the valve tube projecting into the fluid space may be connected to neither of the shell bodies. In this embodiment, the section of the valve tube projecting into the fluid space is therefore freely movable in the fluid space.

Provision can alternatively be made that the section of the valve tube projecting into the fluid space is only connected to one of the shell bodies. In this alternative embodiment, the section of the valve tube projecting into the fluid space is not freely movable in the fluid space, but is rather connected, for example welded, to one of the shell bodies at one side, for example to the outer side of the inner boundary film of the film bag.

The valve is generally a check valve, with a simple flutter valve being preferred. Such a flutter valve, that is optionally flat, can enable a unilateral fluid transfer through the valve tube in a simple manner after introduction of a needle or after an exertion of pressure from the outside.

Provision is made in an embodiment that the valve tube comprises a step at its inner side at which the inner diameter reduces in size in the direction toward the fluid space. The step can have a straight step surface, i.e. a step surface standing normally on the tube axis, but an inclined step surface, i.e. a step surface standing obliquely on the tube axis, is preferred. The step can serve as an abutment to prevent too deep a penetration of a pump needle having a corresponding step at the outer side. The step can be located in the section of the valve tube still connected to both shell bodies, in the section of the valve tube projecting into the fluid space, or in a transition region between these sections.

BRIEF DESCRIPTION OF THE DRAWINGS

Further details and advantages of the invention result from the embodiment described in the following with reference to the Figures. There are shown in the Figures:

FIG. 3: a schematic representation of a patient with a bra and a breast prosthesis on the right side, on the left side, and in both sides of the bra;

FIG. 4: an illustration representation of a routine of a method for a volume adaptation of a breast prosthesis at the user side;

Description of the Preferred Embodiments

Figure 1:
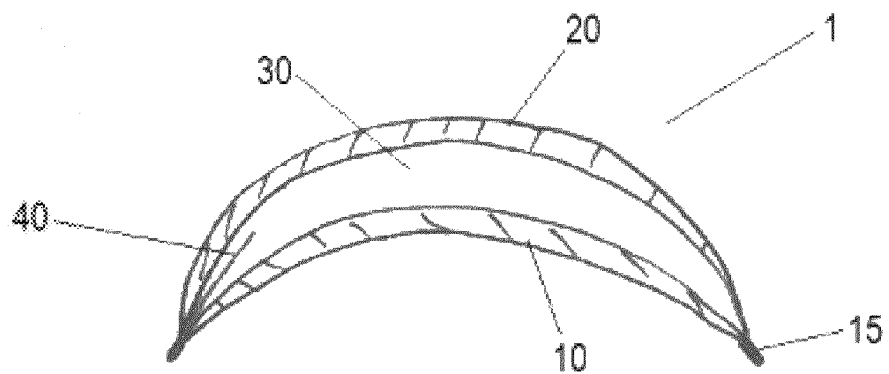
FIG. 1: a schematic representation of a volume-adaptable breast prosthesis in accordance with the invention.

The breast prosthesis 1 in accordance with the invention shown in FIG. 1 having an adaptable volume comprises a first shell body 10 at the lower side of the prosthesis 1 facing the wearer and a second shell body 20 peripherally connected thereto at the upper side of the prosthesis 1 facing away from the wearer. Both shell bodies 10 and 20 are film bags that are filled with a crosslinked two-component silicone rubber compound. The film bags are each produced from two plastic film pieces that are welded to one another along the common peripheral surface.

The shell bodies 10 and 20 are in turn connected along a peripheral weld seam 15 such that a fluid space 30 is formed between them that can, for example, be filled with air, but also with a liquid. The volume of the breast prosthesis 1 can be adapted by filling and emptying the fluid space 30.

To make a subsequent filling and emptying of the fluid space 30 possible, i.e. one taking place after the production, the breast prosthesis 1 comprises a valve tube 40 that is composed of a flexible plastic material and that comprises a flat flutter valve, that penetrates the weld seam 15 in the radial direction, and that is welded between the shell bodies 10 and 20. The valve tube 40 does not only reach up to the end of the weld seam 15, but projects freely, i.e. without being connected to one of the shell bodies 10 or 20, beyond the weld seam 15 into the fluid space 30. The section of the valve tube 40 projecting into the fluid space 30 is therefore freely movable in the fluid space 30.

Figure 2:
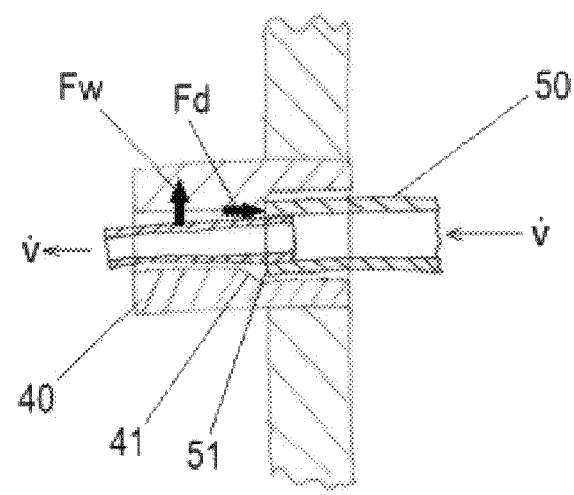
FIG. 2: a plan view of a valve tube of such a breast prosthesis.

A detailed view of the valve tube 40 is shown in FIG. 2. As can be seen from this, the valve tube 40 comprises a step 41 at its inner side at which the inner diameter of the valve tube 40 reduces in size in the direction toward the fluid space.

The step 41 inter alia serves as an abutment to prevent too deep a penetration of a pump needle 50 having a corresponding step 51 at the outer side.

An inherent overpressure protection function for the fluid space 30 is achieved using the design shown to avoid overpumping. Introduced fluid volume V namely produces a pressure increase in the fluid chamber. The channel of the valve tube 40 is widened a little by this pressure (cf. the forces $F_w$ drawn in FIG. 2) and a fluid channel is opened up between the outer surface of the pump needle 50 and the inner surface of the valve tube 40 so that volume can pass to the outside up to and into the region of the corresponding abutments 41 and 51. Further subsequently, the pressure also exerts an outwardly directed compressive force $F_d$ on the step 51 of the pump needle. 50 As soon as this compressive force $F_d$ exceeds the counter frictional forces, the pump needle is pushed a little outward so that a space likewise becomes free between the steps 41 and 51 through which the fluid can ultimately flow back fully outwardly. As soon as the pressure has reduced by a certain degree, the valve tube 40 contracts so much again that the fluid channel between the outer surface of the pump needle 50 and the inner surface of the valve tube 40 is closed and no further pressure drop occurs.

FIG. 3 shows a patient who is wearing a breast prosthesis 1 in accordance with the invention on the right side (FIG. 3a), on the left side (FIG. 3b), or on both sides (FIG. 3c). Provision is made here that the volume-adaptable breast prosthesis 1 can be placed between the skin and the cup of the bra 2. If the bra 2 has integrated pockets, the prosthesis 1 can also be placed therein. The volume-adaptable prosthesis 1 can be continuously increased or decreased in volume in this position by the user 3 or by a further person until the desired volume is reached, for instance based on the feeling of the user 3.

Figure 5:
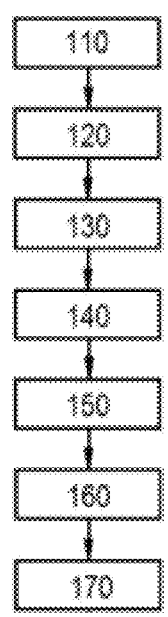
FIG. 5: an associated flowchart.

FIGS. 4-5 show an illustrative representation of a routine of an embodiment variant of a method for volume adaptation and an associated flowchart. In a first step 110, the user 3 who is wearing a bra 2, prepares the volume-adaptable breast prosthesis 1 and a suitable pump accessory 4, for example comprising a pump, a tube, and a needle. In a second step 120, the pump accessory 4 is fastened at a suitable position between the bra 2 and the skin of the patient 3, for example clamped between the straps of the bra 2 and the skin of the patient 3. In a further step 130, the free end of the pump accessory 4, that is, for example, the needle, is connected to the volume-adaptable breast prosthesis 1 in that, for example, the needle is placed into the valve tube. In a next step 140, the bra 2 is opened and the breast area exposed at the side of the bra 2 at which the breast prosthesis 1 should be inserted (in this case at the right from the viewpoint of the wearer). The volume-adaptable breast prosthesis 1 is then placed between the skin of the wearer 3 and the cup of the bra 2 in step 150. In the case of a bra 2 having integrated pockets, the breast prosthesis 1 can also be placed therein. The bra is then closed again and brought into the normal position of wear. Subsequently, in a step 160, the clamped region of the pump accessory 4 is removed using a free hand of the user 3 so that the user 3 can increase or decrease the volume of the breast prosthesis by means of the pump accessory 4. The method ends at step 170 with the finalizing of the increasing or decreasing procedure when the desired size has been reached.

Figure 6:
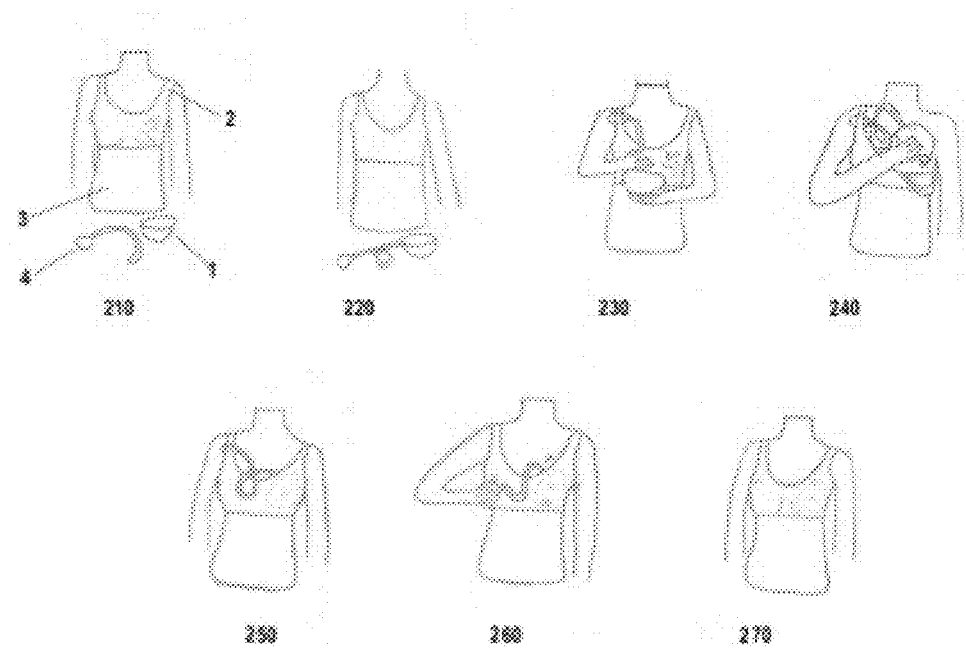
FIG. 6: an illustrative representation of a routine of an alternative method for the volume adaptation of a breast prosthesis in accordance with the invention at the user side.
Figure 7:
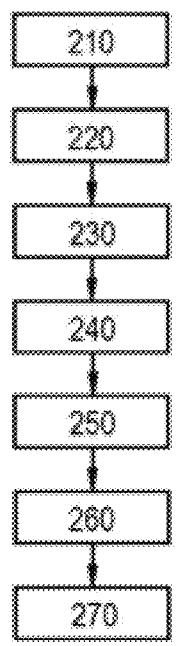
FIG. 7: an associated flowchart.

FIGS. 6-7 show an illustrative representation of a routine of a further embodiment variant of a method for volume adaptation and an associated flowchart. In a first step 210 of this embodiment variant, the user 3, who is wearing a suitable bra 2, prepares the volume-adaptable breast prosthesis 1 and a suitable accessory 4 comprising a pump, a tube, and a cannula. In second step 220, the user 3 connects the pump accessory 4 to the breast prosthesis 1, for example by inserting the needle into the valve tube. The following steps 230-270 correspond to steps 130-170 of the embodiment in accordance with FIGS. 4-5.

The volume adaptation by means of the suitable pump accessory 4 take place as part of both method procedures shown, for example also by the user 3 herself in front of a mirror without any aiding person.

The invention claimed is:

1. A breast prosthesis having an adaptable volume, wherein the breast prosthesis has
    a first shell body,
    a second shell body peripherally connected thereto,
    a fluid space arranged between said shell bodies, and
    a valve tube composed of a flexible material, reaching into the fluid space from the outside in the connection region between the shell bodies, and projecting beyond the connection region into the fluid space,
    the section of the valve tube projecting into the fluid space is at most not connected to only one of the shell bodies,
    the valve tube comprising an internal step where an inner diameter reduces in size in a the radial direction toward the fluid space and having an inclined step surface obliquely extending to an axis of the tube,
    said step positioned inwardly from a weld seam in the radial direction, and arranged as an abutment to prevent too deep penetration of a pump needle, and
    the valve tube is welded between the shell bodies.

2. A breast prosthesis in accordance with claim 1, wherein the first and/or second shell bodies is/are film bags filled with a deformable material.

3. A breast prosthesis in accordance with claim 1, wherein the valve tube comprises a flutter valve.

4. A breast prosthesis in accordance with claim 1, wherein the valve is configured to provide overpressure protection for the fluid space.

5. A breast prosthesis in accordance with claim 4, where the valve is configured to provide said overpressure protection by
    on initial pumping by a pump needle having a corresponding step and inserted into the valve, a channel within the valve is widened,
    subsequently, an outwardly compressive force is directed on the pump needle step,
    when the outwardly directed compressive force exceeds counter friction force, the pump needle is pushed outwardly to free a space between the respective steps of the valve and pump needle through which fluid flows outwardly, and
    when pressure has reduced by a certain degree, the valve tube contracts to close the channel between an outer surface of the pump needle and an inner surface of the valve, with no further pressure drop occurring.

6. A breast prosthesis in accordance with claim 1, in which the section of the valve tube projection into the fluid space is not welded to either of the shell bodies.

7. A breast prosthesis in accordance with claim 1, additionally comprising a pump needle (50) having a corresponding step (51) at an outer side thereof.

* * * * *